United States Patent
Yoshimura et al.

(10) Patent No.: US 10,065,912 B2
(45) Date of Patent: Sep. 4, 2018

(54) METHOD FOR PRODUCING SEVOFLURANE

(71) Applicant: CENTRAL GLASS COMPANY, LIMITED, Ube-shi, Yamaguchi (JP)

(72) Inventors: Takaaki Yoshimura, Yamaguchi (JP); Toshihiko Oono, Yamaguchi (JP); Shinya Akiba, Saitama (JP); Masaki Fujiwara, Tokyo (JP)

(73) Assignee: CENTRAL GLASS COMPANY, LIMITED, Ube-Shi (JP)

( * ) Notice: Subject to any disclaimer, the term of this patent is extended or adjusted under 35 U.S.C. 154(b) by 0 days.

(21) Appl. No.: 15/473,940

(22) Filed: Mar. 30, 2017

(65) Prior Publication Data

US 2018/0222834 A1    Aug. 9, 2018

(30) Foreign Application Priority Data

Feb. 6, 2017  (JP) ................. 2017-019555
Mar. 9, 2017  (JP) ................. 2017-044726

(51) Int. Cl.
*C07C 43/00* (2006.01)
*C07C 41/42* (2006.01)
*C07C 41/22* (2006.01)

(52) U.S. Cl.
CPC .............. *C07C 41/42* (2013.01); *C07C 41/22* (2013.01)

(58) Field of Classification Search
None
See application file for complete search history.

(56) References Cited

U.S. PATENT DOCUMENTS

| | | |
|---|---|---|
| 4,250,334 A | 2/1981 | Coon et al. |
| 4,328,376 A | 5/1982 | Berger et al. |
| 5,679,576 A | 10/1997 | Kawai et al. |
| 5,684,210 A | 11/1997 | Kawai et al. |
| 5,684,211 A | 11/1997 | Kawai et al. |
| 5,763,684 A | 6/1998 | Kawai et al. |
| 5,811,596 A | 9/1998 | Kawai et al. |
| 7,230,142 B1 | 6/2007 | Kawai et al. |
| 2005/0261526 A1 | 11/2005 | Sharratt et al. |

FOREIGN PATENT DOCUMENTS

| | | |
|---|---|---|
| JP | 2786106 B2 | 8/1998 |
| JP | 2786108 B2 | 8/1998 |
| JP | 4087488 B2 | 8/1998 |
| JP | 3240043 B2 | 12/2001 |
| JP | 3441735 B2 | 9/2003 |
| WO | 2007/019161 A2 | 2/2007 |

OTHER PUBLICATIONS

Canadian Office Action issued in Canadian Application No. 2,962,568, dated Jul. 11, 2017.
Dutch Search Report and Written Opinion issued in Dutch Application No. 2018600, dated May 30, 2017, together with an English translation.
Extended European Search Report, dated Nov. 27, 2017, for European Application No. 17163646.7.

*Primary Examiner* — Ana Z Muresan
(74) *Attorney, Agent, or Firm* — Birch, Stewart, Kolasch & Birch, LLP

(57) ABSTRACT

An object of the present invention is to remove a compound A from "sevoflurane containing fluoromethyl-1,1,3,3,3-pentafluoroisopropenyl ether (compound A)" so as to collect high-purity sevoflurane. The present invention concerns a method for producing sevoflurane containing substantially no compound A, comprising the following steps of: bringing a composition containing hydrogen fluoride (HF) and water at a mass ratio of 1:1 to 1:30 into contact with a 1st organic liquid containing sevoflurane and a compound A, thereby obtaining a 2nd organic liquid containing the compound A in an amount that is lower than that in the 1st organic liquid (step 1a); and distilling the 2nd organic liquid under the presence of a degradation inhibitor, thereby obtaining sevoflurane containing substantially no compound A as a main distillation fraction (step 2).

13 Claims, 1 Drawing Sheet

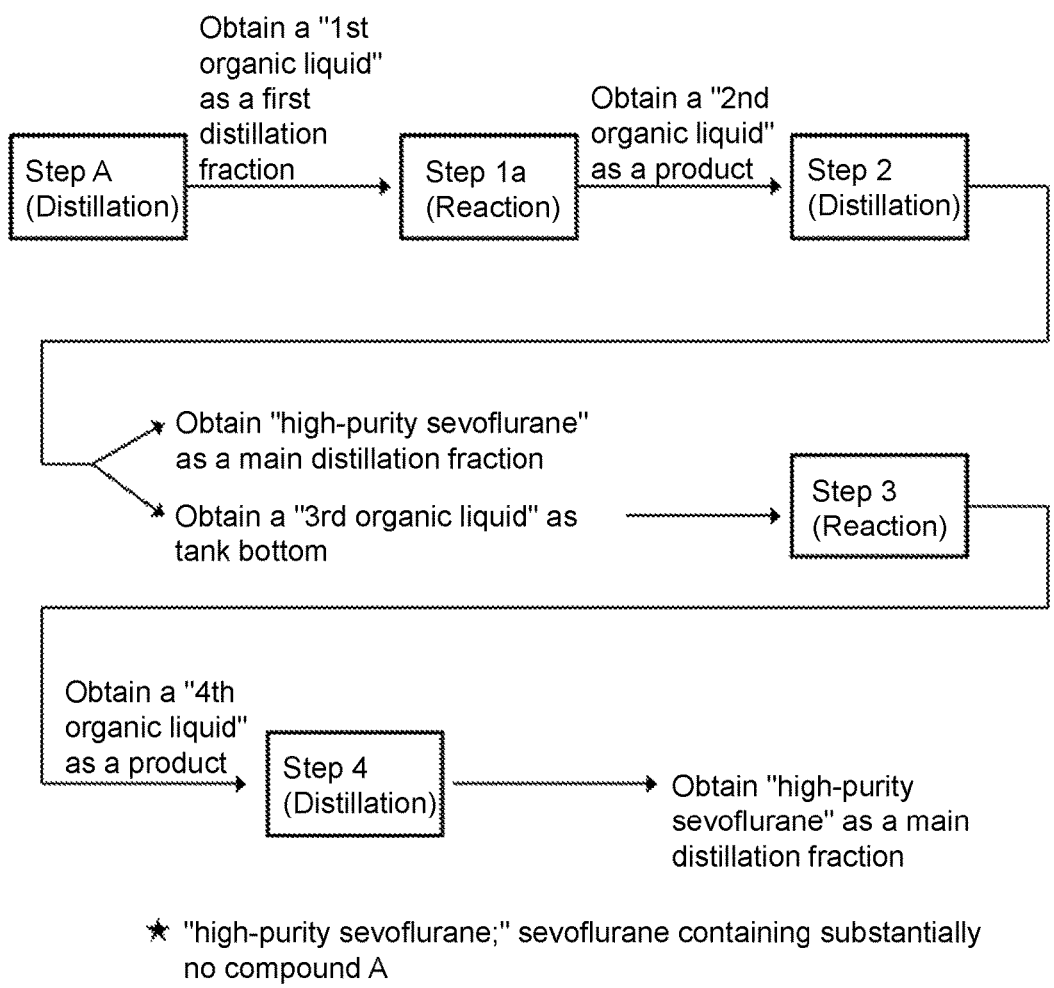

METHOD FOR PRODUCING SEVOFLURANE

TECHNICAL FIELD

The present invention relates to a method for producing fluoromethyl-1,1,1,3,3,3-hexafluoroisopropyl ether (sevoflurane) which has been widely used as medicines and especially inhalation anesthetics.

BACKGROUND ART

Fluoromethyl-1,1,1,3,3,3-hexafluoroisopropyl ether (sevoflurane) has been widely used as a safe inhalation anesthetic for use. As described in U.S. Pat. No. 4,250,334 (Patent Literature 1), sevoflurane can be synthesized by adding concentrated sulfuric acid and hydrogen fluoride to paraformaldehyde, heating the obtained reaction mixture, and adding 1,1,1,3,3,3-hexafluoroisopropyl alcohol (HFIP) dropwise to the mixture. A substance of interest (i.e., sevoflurane) can be collected together with an unreacted substance (e.g., HFIP) by collecting a gas generated in the reaction system.

Various by-products are generated in the above sevoflurane synthesis reaction. Of these, a by-product that is difficult to separate is bis(fluoromethyl)ether. However, it has been reported that bis(fluoromethyl)ether can be efficiently removed by bringing a reaction mixture of sevoflurane into contact with "Brønsted acid such as concentrated sulfuric acid, Lewis acid, or an acid immobilized to a resin or the like" (Patent Literature 2: JP Patent No. 2786106). Alternatively, bis(fluoromethyl)ether can be efficiently removed by bringing it into contact with zeolite (Patent Literature 3: JP Patent No. 3240043).

In addition, it is known that unreacted HFIP can be efficiently removed by bringing an organic layer containing sevoflurane into "contact with an basic aqueous solution of sodium hydroxide or the like" (Patent Literature 4: JP Patent No. 4087488).

Another by-product contained in sevoflurane is fluoromethyl-1,1,3,3,3-pentafluoroisopropenyl ether (generally referred to as "compound A"). This compound is regarded as a compound that is generated when sevoflurane undergoes a dehydrofluoriation reaction. When sevoflurane is brought into contact with a strong base such as sodium hydroxide, a small amount of this compound might be generated. In addition, it is gradually generated during distillation and purification of sevoflurane (see the following formula).

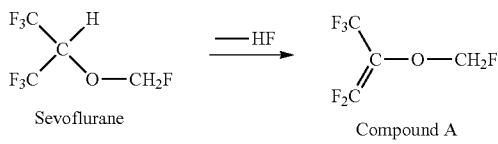

Sevoflurane                    Compound A

The compound A itself is a stable compound so that it is not easily degraded even when heated. In addition, it shows pseudoazeotropic behavior together with sevoflurane. For such reason, once the compound A is generated during purification of sevoflurane, it often becomes difficult to separate the compound A from sevoflurane (purification of sevoflurane).

As a technique for solving such problem, JP Patent No. 2786108 (Patent Literature 5) describes attempts made to conduct "distillation and purification under the presence of a degradation inhibitor such as sodium hydrogen phosphate." It has been revealed that a reaction for degrading sevoflurane into the compound A during distillation can be remarkably inhibited by such technique, and a small amount of the compound A is mainly concentrated in a first distillation fraction so that sevoflurane obtained as a main distillation fraction contains substantially no compound A. As a result, sevoflurane containing the compound A at a level not greater than the detection limit was successfully obtained as a main distillation fraction.

CITATION LIST

Patent Literature

Patent Literature 1: U.S. Pat. No. 4,250,334
Patent Literature 2: JP Patent No. 2786106
Patent Literature 3: JP Patent No. 3240043
Patent Literature 4: JP Patent No. 4087488
Patent Literature 5: JP Patent No. 2786108

SUMMARY OF INVENTION

Technical Problem

The method of Patent Literature 5 is an excellent method whereby generation of the compound A as a by-product upon distillation and purification of sevoflurane is inhibited so that a main distillation fraction (sevoflurane fraction) obtained through distillation does not contain the compound A. In other words, as disclosed in Examples 2-No. 1, No. 2 of Patent Literature 5, when crude sevoflurane containing the compound A at 10 to 30 ppm is distilled with the addition of sodium phosphate dibasic as a degradation inhibitor, sevoflurane containing substantially no compound A (meaning that the compound A is contained at less than 1 ppm; the same applies hereafter) can be obtained as a main distillation fraction while the compound A is mainly concentrated in a first distillation fraction.

However, the above method is disadvantageous in that loss of sevoflurane is likely to occur. In other words, as stated above, the compound A shows pseudoazeotropic behavior together with sevoflurane. Therefore, when "sevoflurane containing a compound A" is distilled in accordance with Patent Literature 5, it is inevitable that a part of sevoflurane is distilled in a first distillation fraction together with the compound A. More specifically, according to Example 2-No. 1, No. 2 of Patent Literature 5, generation of the compound A during distillation can be significantly inhibited. Meanwhile, the distillation yield (the recovery rate of sevoflurane as a main distillation fraction) remains at a level of 71% to 72%. On the other hand, the amount of the "first distillation fraction" accounts for as high as 10% of the recovered amount of the "main distillation fraction." The content of sevoflurane in the first distillation fraction actually reaches 99.6% to 99.8%. As a result, the "first distillation fraction" mainly consists of sevoflurane, resulting in "loss of a relatively large amount of sevoflurane for separation of a small amount of the compound A."

Under the above circumstances, the present inventors made attempts to subject a "first distillation fraction" obtained by the above method directly to precise distillation again so as to isolate sevoflurane. As a result, however, when distillation was conducted at the same number of theoretical stages and the same reflux ratio, the compound A was continuously detected from the start to almost the end of distillation (in other words, the peak area did not decrease to a level of less than 1 ppm upon FID gas chromatography analysis) (see "Comparative Example 1"). Meanwhile, by conducting distillation again with an increased number of theoretical stages compared with that for collection of the first distillation fraction, a first distillation fraction, in which the compound A was further concentrated, could be recovered, making it possible to obtain a small amount of sevoflurane containing substantially no compound A as a main distillation fraction. However, such technique requires the use of a plurality of distillation columns under different conditions, and merely causes the operation to be complicated. Thus, such method cannot be regarded as a method for efficiently obtaining high-purity sevoflurane.

Meanwhile, the compound A, which is a substance that causes reduced efficiency of distillation, has a structure in which sevoflurane is dehydrofluorinated. It was therefore considered that if HF is allowed to act on the compound A, the compound A would be converted to sevoflurane with the addition of HF (see the following formulae).

Compound A+HF (anhydrous)→Sevoflurane

Compound A+HF (anhydrous)+Concentrated sulfuric acid→Sevoflurane

However, even though anhydrous HF was allowed to act on the compound A, the above addition reaction did not proceed. Even in a system in which concentrated sulfuric acid was added as a reaction accelerator, the reaction did not proceed as expected.

As described above, a novel method whereby a compound A can be removed from "sevoflurane containing a compound A" so that high-purity sevoflurane can be recovered has been awaited.

Solution to Problem

As a result of intensive studies in order to achieve the above object, the present inventors found that by bringing a compound A into contact with a "composition containing hydrogen fluoride (HF) and water at a mass ratio of 1:1 to 1:30," it is possible to allow the compound A to gradually react so as to be converted to a chemical species (herein referred to as "compound X") having an unspecified structure, which can be separated from sevoflurane via distillation.

Hitherto, a specific molecular structure of the "compound X" has not been identified. However, the present inventors confirmed a phenomenon that when 1,2-dichloroethane (sometimes herein abbreviated as "DCE") is allowed to coexist as an internal standard substance and brought into contact with the above composition, the gas chromatography area of the compound A with respect to that of DCE decreases over time (see "Example 1" below). This undoubtedly suggests that a chemical reaction is induced during the operation, resulting in reduction of the content of the compound A. Originally, the compound A is not a compound that can be easily degraded when heated. In addition, the compound A does not cause the above additional reaction even when brought into contact with anhydrous HF. That is, the fact that a chemical reaction between the compound A and a liquid containing water as a main component takes place at a relatively low temperature around room temperature (this reaction is herein referred to as "step 1").

Based on the above finding, the present inventors brought "sevoflurane containing a small amount of a compound A" into contact with a "composition containing hydrogen fluoride (HF) and water at a mass ratio of 1:1 to 1:30." As a result, there was a significant decrease in the amount of the compound A with respect to the amount of coexisting sevoflurane over time, suggesting that sevoflurane is stable under such conditions while the compound A selectively causes a chemical reaction (this reaction step is herein referred to as "step 1a").

Next, the organic layer after the termination of step 1a was separated from the aqueous layer (of a composition of HF and water), treated with water washing, and subjected to precise distillation under the presence of a degradation inhibitor. As a result, "sevoflurane containing substantially no compound A (this means that the peak area ratio of FID gas chromatography corresponds to a concentration of less than 1 ppm; the same applies hereafter)" was successfully obtained as a main distillation fraction component in an amount that was remarkably greater than that in the case of not conducting the above step 1a (step 2).

Further, a liquid remaining in the form of residues remaining after distillation (or tank bottom) obtained as a result of step 2 was analyzed. Unexpectedly, the liquid was found to contain "polyether" expressed by the following formula:

$R^1O(CH_2O)_nR^2$ (where $R^1$ and $R^2$ each independently represent hydrogen, a $C_1$ to $C_{10}$ alkyl group, or a haloalkyl group (halogen: fluorine, chlorine, or bromine), n is an integer of 1 to 10, and $R^1$ and $R^2$ do not represent hydrogen at the same time).

The most typical examples of chemical species of the above polyether are "polyether 1" and "polyether 2" specified below. Residues remaining after distillation (tank bottom residues) after the termination of step 2 tend to contain large amounts of these generated polyethers (see the Examples below).

$(CF_3)_2CH—CH_2—O—CH(CF_3)_2$ <Polyether 1>

1,1,1,3,3,3-Hexafluoro-2-[[2,2,2-trifluoro-1-(trifluoromethyl)ethoxy]methoxy] propane $(CF_3)_2CHO—CH_2—O—CH_2—O—CH(CF_3)_2$ <Polyether 2>

2,2'-[Oxybis(methyleneoxy)]bis[1,1,1,3,3,3-hexafluoropropane]

"Polyether 3" and "polyether 4" may be generated, in addition to or instead of the above polyethers, depending on the time or temperature of distillation in step 2.

$(CF_3)_2CHO—(CH_2—O)_3—CH(CF_3)_2$ <Polyether 3>

2,2'-[Oxytris(methyleneoxy)]bis[1,1,1,3,3,3-hexafluoropropane]

$(CF_3)_2CHO—(CH_2—O)_4—CH(CF_3)_2$ <Polyether 4>

2,2'-[Oxytetora(methyleneoxy)]bis[1,1,1,3,3,3-hexafluoropropane]

Such "polyether" is not a compound that is generated by bringing sevoflurane into contact with a "composition containing hydrogen fluoride (HF) and water at a mass ratio of 1:1 to 1:30." In view of this, it is presumed that the "polyether" is from the "compound X" generated as a result of step 1, and therefore, the compound X induces some kind of chemical reaction during distillation, which results in generation of the polyether.

Here, it is known that the "polyether" (regardless of the integer represented by n) can be converted to sevoflurane when brought into contact with HF and a reaction accelerator (particularly preferably concentrated sulfuric acid) (JP Patent No. 3441735). Based on this finding, the present inventors confirmed generation of sevoflurane at a significant level by allowing HF and concentrated sulfuric acid to act on residues (tank bottom) remaining after step 2 (distillation step) of the present invention. In other words, if desired, it is possible to convert tank bottom residues remaining after step 2 to sevoflurane by allowing the residues to react with HF and concentrated sulfuric acid (this reaction step is referred to as "step 3"). It is possible to obtain sevoflurane as a main distillation fraction by distilling crude sevoflurane obtained in step 3 ("step 4").

It is possible to reduce a compound A in a "mixed composition of sevoflurane and a compound A" so as to collect "sevoflurane containing substantially no compound A" by conducting "step 1a" and "step 2" in combination. It is also possible to effectively utilize residues (tank bottom residues or tank bottom) remaining after "step 2" by further conducting "step 3" and "step 4" in combination. Accordingly, an embodiment in which all of step 1a, step 2, step 3, and step 4 are combined is particularly preferable embodiment of the present invention.

As described above, the present inventors found that a compound A can be converted to a compound X under specific conditions (step 1). Based on the finding, the present inventors found each of steps 1a to 4 described above. As a result, the present inventors succeeded in remarkably suppressing "loss of sevoflurane upon removal of a compound A from sevoflurane via distillation," which is particularly problematic in the method of Patent Literature 5. In a more preferable embodiment, it has become possible to convert a "compound X" contained in tank bottom residues remaining after step 2, which is an intermediate product from a compound A, to sevoflurane. As a result, a method for producing sevoflurane, which has been remarkably improved compared with conventional methods, can be provided.

Specifically, the present invention encompasses the following inventions.

[Invention 1]

A method for reducing the amount of a compound A, comprising the following step:

step 1 of bringing fluoromethyl-1,1,3,3,3-pentafluoroisopropenyl ether (compound A) into contact with a composition containing hydrogen fluoride and water at a mass ratio of 1:1 to 1:30.

[Invention 2]

A method for producing a 2nd organic liquid, comprising the following step:

step 1a of bringing a liquid (1st organic liquid) containing sevoflurane and fluoromethyl-1,1,3,3,3-pentafluoroisopropenyl ether (compound A) into contact with a composition containing hydrogen fluoride and water at a mass ratio of 1:1 to 1:30, thereby, obtaining the following liquid (i) or (ii) (2nd organic liquid): (i) an organic liquid containing sevoflurane and the compound A in an amount that is lower than that in the 1st organic liquid; or (ii) an organic liquid containing sevoflurane and substantially no compound A.

[Invention 3]

The method according to Invention 2, wherein the temperature during the contact is 0° C. to 60° C.

[Invention 4]

The method according to Invention 2 or 3, wherein the contact is made under the coexistence of hexafluoroisopropyl alcohol (HFIP).

[Invention 5]

A method for producing sevoflurane containing substantially no compound A, comprising the following step:

step 2 of distilling the 2nd organic liquid obtained by the method according to any one of claims 2 to 4 under the presence of a degradation inhibitor, thereby obtaining the sevoflurane containing substantially no compound A as a main distillation fraction.

[Invention 6]

The method according to Invention 5, wherein the degradation inhibitor used in step 2 is at least one member selected from the group consisting of $NaHCO_3$, $Na_2B_4O_7$, $H_3BO_4$, $C_6H_4(COOK)(COOH)$, $Na_2SO_3$, $Na_2HPO_4$, $CH_3COONa$, and $Na_3PO_4$.

[Invention 7]

The method according to Invention 5 or 6, further comprising the following step:

step 3 of bringing anhydrous hydrogen fluoride and a reaction accelerator into contact with residues (3rd organic liquid) remaining after distillation in the step 2, thereby obtaining a liquid (4th organic liquid) in which at least a part of a component in the 3rd organic liquid is converted to sevoflurane.

[Invention 8]

The method according to Invention 7, further comprising the following step:

step 4 of distilling the 4th organic liquid so as to obtain sevoflurane containing substantially no compound A as a main distillation fraction.

[Invention 9]

The method according to any one of Inventions 2 to 8, wherein the "1st organic liquid" is obtained as a first distillation fraction in the following step:

step A of distilling sevoflurane under the presence of a degradation inhibitor so as to collect the first distillation fraction.

[Invention 10]

The method according to Invention 9, wherein the degradation inhibitor used in step A is at least one member selected from the group consisting of $NaHCO_3$, $Na_2B_4O_7$, $H_3BO_4$, $C_6H_4(COOK)(COOH)$, $Na_2SO_3$, $Na_2HPO_4$, $CH_3COONa$, and $Na_3PO_4$.

[Invention 11]

A method for producing sevoflurane containing substantially no compound A, comprising the following steps:

step 1b of bringing a liquid (1st organic liquid) containing sevoflurane and fluoromethyl-1,1,3,3,3-pentafluoroisopropenyl ether (compound A)" into contact with a composition containing hydrogen fluoride (HF) and water at a mass ratio of 1:1 to 1:30 under the presence of hexafluoroisopropyl alcohol (HFIP) at 0° C. to 60° C., thereby obtaining the following liquid (i) or (ii) (2nd organic liquid): (i) an organic liquid containing sevoflurane and the compound A in an amount that is lower than that in the 1st organic liquid; or (ii) an organic liquid containing sevoflurane and substantially no compound A; and step 2 of distilling the 2nd organic liquid under the presence of a degradation inhibitor, thereby obtaining the sevoflurane containing substantially no compound A as a main distillation fraction.

[Invention 12]

The method according to Invention 11, further comprising the following steps:

step 3 of bringing residues (3rd organic liquid) remaining after distillation in step 2 into contact with anhydrous hydrogen fluoride and a reaction accelerator, thereby obtaining a liquid (4th organic liquid) in which at least a part of the 3rd organic liquid is converted to sevoflurane; and step 4 of distilling the 4th organic liquid under the presence of a degradation inhibitor, thereby obtaining sevoflurane containing substantially no compound A as a main distillation fraction.

Advantageous Effects of Invention

The present invention is advantageous in that a compound A can be converted to a compound X, which can be easily separated from sevoflurane (step 1).

In addition, in another embodiment, the present invention is advantageous in that it is possible to selectively allow the compound A in a "1st organic liquid" to react, thereby producing a "2nd organic liquid" containing a reduced content of the compound A or containing substantially no compound A (step 1a).

Further, in still another embodiment, the present invention is advantageous in that it is possible to produce sevoflurane containing substantially no compound A at a significantly large amount compared with the case of not conducting step 1a using, as a raw material, the "1st organic liquid" which has been conventionally difficult to effectively use (step 1a and step 2).

Furthermore, in still another embodiment, the present invention is further advantageous in that the it is surprisingly possible to produce sevoflurane using, as a raw material, residues (tank bottom) remaining after distillation in step 2 (step 1a and steps 2 to 4).

According to the present invention, it becomes possible to produce sevoflurane using, as a starting material, "sevoflurane containing a compound A (1st organic liquid)" which has been difficult to effectively utilize, thereby providing an improved method for producing sevoflurane.

BRIEF DESCRIPTION OF DRAWINGS

FIG. 1 illustrates a chart of relationship among the following technical terms used herein: "step A," "step 1a," "step 2," "step 3," "step 4," "1st organic liquid," "2nd organic liquid," "3rd organic liquid," and "4th organic liquid."

DESCRIPTION OF EMBODIMENTS

Hereafter, the present invention is described in detail. The scope of the present invention is not limited thereto. The present invention may be carried out with appropriate changes without departing from the purport of the present invention.

This description includes part or all of the content as disclosed in the description and/or drawings of Japanese Patent Application No. 2017-019555, which is a priority document of the present application. All publications, including prior art documents, patent applications, patent publications, and other patent documents cited herein, are incorporated herein by reference in their entirety.

The technical terms and expressions used herein are defined as below.

"Step 1:"

Step 1 is a step of bringing fluoromethyl-1,1,3,3,3-pentafluoroisopropyl ether (referred to as "compound A") into contact with a "composition containing hydrogen fluoride (HF) and water at a mass ratio of 1:1 to 1:30" (thereby making it possible to convert the compound A into a compound X to reduce the amount of the compound A).

"Step A:"

Step A is a step of distilling sevoflurane under the presence of a degradation inhibitor, thereby collecting a first distillation fraction (the first distillation fraction collected in the step A is used as a "1st organic liquid" in step 1a in a particularly preferable embodiment of the present invention).

"Step 1a:"

Step 1a is a step of bringing the "liquid (1st organic liquid) containing sevoflurane and fluoromethyl-1,1,3,3,3-pentafluoroisopropyl ether (hereafter referred to as "compound A")" into contact with a "composition containing hydrogen fluoride (HF) and water at a mass ratio of 1:1 to 1:30," thereby obtaining a "2nd organic liquid." Specifically, step 1a may be a step of causing the compound A to react as a result of the contact so as to convert the "1st organic liquid" into the "2nd organic liquid" (step 1a is particularly characterized in that the "1st organic liquid" is used as a reaction material in step 1) (note that the "2nd organic liquid" means: (i) an organic liquid containing sevoflurane and the compound A in an amount that is lower than that in the "1st organic liquid;" or (ii) an organic liquid containing sevoflurane and substantially no compound A; the same applies hereafter).

"Step 1b:"

Step 1b is a step of bringing the "1st organic liquid containing sevoflurane and fluoromethyl-1,1,3,3,3-pentafluoroisopropyl ether (hereafter referred to as "compound A")" into contact with a "composition containing hydrogen fluoride (HF) and water at a mass ratio of 1:1 to 1:30" under the presence of hexafluoroisopropyl alcohol (HFIP) at 0° C. to 60° C., thereby obtaining a "2nd organic liquid." Specifically, step 1b may be a step of causing the compound A to react as a result of the contact so as to convert the "1st organic liquid" to a "2nd organic liquid".

In addition, step 1b is a particularly preferable embodiment of step 1a. When it is necessary to distinguish step 1b from step 1a with a wider concept, the above step is called "step 1b;" however, the explanation of step 1a may directly apply to step 1b, unless otherwise specified.

"Step 2:"

Step 2 is a step of distilling the "2nd organic liquid" obtained in step 1a (or step 1b) under the presence of a degradation inhibitor, thereby obtaining sevoflurane containing substantially no compound A as a distillation fraction.

"Step 3:"

Step 3 is a step of bringing anhydrous HF and a reaction accelerator into contact with residues (or tank bottom which is referred to as a "3rd organic liquid") remaining after step 2, thereby obtaining a liquid (4th organic liquid) in which at least a part of a component in the "3rd organic liquid" is converted to sevoflurane.

"Step 4:"

Step 4 is a step of distilling the "4th organic liquid" under the presence of a degradation inhibitor, thereby obtaining sevoflurane containing substantially no compound A as a main distillation fraction.

"1st organic liquid:"

A 1st organic liquid is a liquid composition containing sevoflurane and a compound A.

"2nd organic liquid:"

A 2nd organic liquid is a composition obtained by subjecting the 1st organic liquid to step 1a (or step 1b), which is: (i) an organic liquid containing sevoflurane and the compound A in an amount that is lower than that in the "1st organic liquid;" or (ii) an organic liquid containing sevoflurane and substantially no compound A.

"3rd organic liquid:"

A 3rd organic liquid corresponds to residues (or tank bottom) remaining after distillation in step 2 (note that this 3rd organic liquid unexpectedly contains "polyether").

"4th organic liquid:"

A 4th organic liquid is an organic liquid obtained in step 3, which contains at least sevoflurane.

"Containing substantially no compound A:"

The expression "containing substantially no compound A" means that the concentration of a compound A in a liquid of interest calculated based on peak area is less than 1 ppm upon FID gas chromatography analysis.

Hereafter, the above steps are described in detail in the approximate order of operations.

[1] Step 1

Step 1 is a step of bringing a compound A into contact with a "composition containing hydrogen fluoride (HF) and water at a mass ratio of 1:1 to 1:30." Accordingly, the compound A is allowed to react so that a "compound X" having an unspecified structure can be obtained (it can be converted to a "compound X").

As described above, a small amount of the compound A may be produced by bringing sevoflurane into contact with a base such as sodium hydroxide. In addition, the compound A is gradually generated during distillation and purification of sevoflurane. An authentic preparation of the compound A (compound A having purity 99% or more) can be obtained by allowing sevoflurane to react with lithium bis(trimethylsilyl)amide serving as a superbase in an anhydrous tetrahydrofuran solvent at −70° C. to −60° C., followed by distillation and purification (Example 1 described below is an experimental example using this authentic preparation) in accordance with Journal of Fluorine Chemistry, vol. 45 (2), November 1989, P. 239 to P. 253.

It is possible to conduct step 1 by allowing hydrogen fluoride (HF) and water to act on a compound A (liquid). The order of bringing three chemical species (compound A, hydrogen fluoride, and water) into contact with one another is not particularly limited. However, it is particularly preferable to mix hydrogen fluoride and water in advance to prepare "hydrofluoric acid" and then bring hydrofluoric acid into contact with the compound A in view of the ease of handling.

Here, the expression "composition containing hydrogen fluoride (HF) and water at a mass ratio of 1:1 to 1:30" means that the composition containing these two chemical species at such mass ratio. It is also possible to allow other chemical species (e.g., sevoflurane, HFIP, or sulfuric acid) to coexist.

The reaction in step 1 does not proceed under anhydrous conditions (that is to say, when anhydrous hydrogen fluoride is used). Therefore, water must be present in an amount 1-fold by mass or more that of hydrogen fluoride. Meanwhile, when water is present in an amount more than 30-fold by mass that of hydrogen fluoride, hydrogen fluoride is excessively diluted, which prevents the reaction from proceeding to a sufficient extent. In other words, "a mass ratio of hydrogen fluoride (HF) and water of 1:1 to 1:30" is a requirement of step 1.

In particular, when the "mass ratio of hydrogen fluoride (HF) and water" is 1:1 to 1:10, reactivity of the compound A becomes remarkably high, which is particularly preferable.

Meanwhile, the "mass ratio of a compound A and hydrogen fluoride" is not particularly limited. When the amount of hydrogen fluoride is too small, it decelerates the reaction rate. When the amount of hydrogen fluoride per 1 g of the compound A is 1 g or more, the reaction rate tends to increase, which is preferable. In particular, when the amount of hydrogen fluoride per 1 g of the compound A is 4 g or more, the reaction proceeds very rapidly, which is particularly preferable.

Note that the reaction in step 1 also depends on the concentration of the compound A in a reaction system. As described in "step 1a (which is one embodiment of step 1)" below, even if even the content of hydrogen fluoride is 4 times that of the compound A, for example, a reaction solution is formed with "a large amount of sevoflurane" and "a small amount of (e.g., 1000 ppm (0.1%) or less) a compound A," the reaction rate might not increase to a sufficient extent when the concentration of the compound A is too low. In such case, as described in the Examples below, it is preferable that the mass ratio of the compound A and HF is 1:100 or more. In a case in which the amount of the compound A is obviously small (at the ppm level), the mass ratio may be increased to a high level of, for example, $1:10^3$ to $1:10^6$. As stated above, the mass ratio of the compound A and HF is not necessarily univocally determined. It should be noted that even if HF or water is present in an amount that is remarkably greater than that of the compound A, it does not result in inhibition of the reaction or induction of a new side reaction. It is therefore desirable that those skilled in the art can appropriately determine and change the amounts of HF and water to be used so as to optimize conditions that readily allow the compound A to react when conducting this step.

A reaction container lined with stainless steel, iron, a fluorine resin, or the like is preferably employed as a reactor in step 1. As hydrogen fluoride is used, a glass reaction container is inappropriate.

In step 1, it is preferable to perform stirring in order to efficiently bring a compound A (an organic layer) into contact with an "aqueous layer containing water and HF." A specific stirring technique is not limited. A motor-driven rotary stirrer can be preferably used at a mass-production scale. It is also possible to use a magnetic stirrer at a laboratory scale. In addition to a method using a "stirrer," it is possible to employ a method wherein a reactor itself is shaken or a method wherein an organic layer and an aqueous layer are mixed by transferring a reaction solution (for example, a reaction solution is allowed to pass through a tube). These methods also corresponds to "stirring" in step 1 of the present invention.

The reaction temperature in step 1 (temperature during the above contact) is not particularly limited; however, it is preferably 0° C. to 60° C. When it is below 0° C., the reaction rate is decelerated. When it is above 60° C., hydrofluoric acid tends to volatize, resulting in complicated handling. The reaction temperature in step 1 is more preferably 15° C. to 45° C. and particularly preferably 25° C. to 40° C. When the reaction temperature is within such temperature range, the reaction is allowed to relatively smoothly proceed in step 1 and handling is improved.

It is preferable to conduct the reaction in step 1 under tight sealing conditions. Alternatively, it is possible to conduct the reaction under open conditions when using a system capable of collecting and removing a volatizing by-product.

A reaction product (compound X) in step 1 has not been identified. It might be of a chemical species that is difficult to capture by gas chromatograph analysis. Note that as a result of observation by the present inventors, no solid component (insoluble component) is generated throughout this step, and an organic layer usually remains transparent before and after the reaction. Accordingly, it is possible to predict the status of progress in the reaction by allowing a standard substance that is inert to react (e.g. 1,2-dichloroethane (DCE)) with a compound A to coexist so as to determine the ratio of gas chromatography areas of the compound A and DCE. This is a particularly preferable method for understanding the reaction progress status.

The time required for step 1 varies depending on conditions; however, it is typically 10 minutes to 12 hours (720 minutes). It is not necessary to continue the reaction in step 1 to achieve a conversion rate of 100%. If it is possible to degrade at least a part of the compound A, it would be advantageous for the subsequent collection of sevoflurane with respect to the amount of the compound A degraded. Therefore, the conversion rate in the reaction in step 1 is not necessarily strictly determined. In a preferable example, step 1 is terminated after the elapse of a certain period of time (e.g., 1 to 5 hours). The reaction time for step 1 may be appropriately determined in consideration of the time required for conducting other steps for producing sevoflurane (the reaction step and the purification step).

In addition to an unreacted compound A, a small amount of a low-molecular-weight product might be confirmed in the organic layer after the termination of step 1. However, it is usually impossible to detect "polyether" that is to be present in residues (tank bottom) after step 2 described below. In addition, sevoflurane is not significantly generated in this step, and even if sevoflurane can be detected, the amount thereof usually remains at a level of trace or less.

[2] Step A (Distillation in Step A)

Step A is a step of distilling sevoflurane under the presence of a degradation inhibitor so as to collect a "first distillation fraction" prior to step 1a described below.

A "first distillation fraction" collected in step A is a liquid composition containing sevoflurane and a compound A. In the present invention, it is preferable to use the first distillation fraction as a "1st organic liquid" in step 1a in view of the object of the present invention (distillation in this step is hereafter sometimes referred to as "distillation in step A" so as to be distinguished from other distillation steps of the present invention).

Sevoflurane can be preferably synthesized in accordance with Patent Literature 1 and purified by the methods disclosed in Patent Literature 2 to 4. "Distillation" performed in accordance with Patent Literature 5 following the purification method (or before or after the purification method) corresponds to "distillation in step A."

Note that the main purpose of Patent Literature 5 and "step 2" and "step 4" described below is to collect a "main distillation fraction" that corresponds to "sevoflurane containing substantially no compound A." Meanwhile, "distillation in step A" is characterized by collecting a "first distillation fraction" that corresponds to "sevoflurane containing a compound A."

A degradation inhibitors that can be used for "distillation in step A" is hydroxide, hydrogen phosphate, phosphate, hydrogen carbonate, borate, or sulfite of an alkaline metal, an alkaline metal salt of acetic acid or phthalic acid, or boric acid as disclosed in Patent Literature 5. Examples of hydroxide of an alkaline metal include NaOH and KOH. Hydrogen phosphate of an alkaline metal is hydrogen phosphate or dihydrogen phosphate of an alkaline metal. Specific examples thereof include $Na_2HPO_4$, $NaH_2PO_4$, $K_2HPO_4$, and $KH_2PO_4$. Examples of phosphate of an alkaline metal include metaphosphate or polyphosphate of an alkaline metal as well as orthophosphate of an alkaline metal. Specific examples thereof include $Na_3PO_4$, $K_3PO_4$, $(NaPO_3)_3$, $(NaPO_3)_4$, $(KPO_3)_3$, and $(KPO_3)_4$. Examples of hydrogen carbonate of an alkaline metal include $NaHCO_3$ and $KHCO_3$. Examples of borate of an alkaline metal include diborate, metaborate, tetraborate, pentaborate, hexaborate, and octaborate of an alkaline metal. Specific examples thereof include $NaBO_2$, $Na_2B_4O_7$, $NaB_5O_8$, $Na_2B_6O_{10}$, $Na_2B_8O_{18}$, $Na_4B_2O_5$, $KBO_2$, $K_2B_4O_7$, $KB_5O_8$, $K_2B_6O_{10}$, and $K_2B_8O_{18}$. Examples of sulfite of an alkaline metal include $Na_2SO_3$ and $K_2SO_3$. In addition, examples of an alkaline metal salt of acetic acid include $CH_3COONa$ and $CH_3COOK$.

Examples of an alkaline metal salt of phthalic acid include alkaline metal salts of o-phthalic acid, m-phthalic acid, and p-phthalic acid. Specific examples thereof include o-$C_6H_4$(COOK)(COOH), m-$C_6H_4$(COOK)(COOH), p-$C_6H_4$(COOK)(COOH), o-$C_6H_4$(COONa)(COOH), m-$C_6H_4$(COONa)(COOH), and p-$C_6H_4$(COONa)(COOH). Among the additives described above, examples of particularly preferable additives having an effect of strongly preventing degradation of sevoflurane include $NaHCO_3$, $Na_2B_4O_7$, $H_3BO_4$, $C_6H_4$(COOK)(COOH), $Na_2SO_3$, $Na_2HPO_4$, $CH_3COONa$, and $Na_3PO_4$. Of these, $H_3BO_4$, $C_6H_4$(COOK)(COOH), $Na_2HPO_4$, $CH_3COONa$, and the like having more excellent effects are more preferable additives.

A degradation inhibitor may be directly added in a solid state. In such case, the amount to be added is appropriately 0.01% by mass to 10% by mass, preferably 0.05% by mass to 5% by mass, and more preferably 0.1% by mass to 1% by mass with respect to the amount of sevoflurane to be treated.

It is also possible to add a degradation inhibitor in the form of an aqueous solution. In such case, the concentration thereof is not particularly limited; however, it is appropriately 0.01% by mass to a level of saturation (saturated solution), preferably 0.1% by mass to 10% by mass, and more preferably 1% by mass to 5% by mass. In addition, the amount of a degradation inhibitor added in the form of an aqueous solution is not particularly limited, and thus, an appropriate amount to be added may be selected depending on the concentration of the aqueous solution. For example, when the concentration of the aqueous solution is set to 1% by mass, the amount is appropriately 1% by mass to 200% by mass, preferably 3% by mass to 100% by mass, and more preferably 5% by mass to 50% by mass with respect to sevoflurane to be treated.

Sevoflurane that is a raw material for distillation in step A may contain impurities or a compound A (note that the use of purified sevoflurane containing substantially no compound A is not particularly limited). Also, in the case of distillation under the presence of any degradation inhibitor described above, a small amount of compound A can be generated in a tank. When distillation is performed under such conditions, a compound A as a whole is collected as a "first distillation fraction," making it substantially possible to avoid incorporation of the compound A in a "main distillation fraction." However, as stated above, it is impossible to prevent sevoflurane from being contained in the first distillation fraction even by such distillation operation in which a degradation inhibitor is allowed to coexist.

A distillation column used for distillation in step A is not particularly limited. However, a distillation column filled with a structured packing or a non-structured packing can be preferably used. Examples of a structured packing include Sulzer packing, Mellapack, Techno-pack, and Flexi-pack. Examples of a non-structured packing include Heli-pack, Raschig ring, and Dixon packing.

The number of theoretical stages for distillation in step A is not particularly limited; however, it may be 2 to 50. In particular, it is preferably 3 to 30 and more preferably 5 to 20.

The reflux ratio is usually 0.5 to 50, preferably 1 to 30, and more preferably 1 to 20.

Pressure applied during distillation in step A is not particularly limited. It is easy and preferable to perform distillation at ordinary pressure. In such case, as a main component to be distilled is sevoflurane, the distillation temperature (column top temperature) upon collection of a main distillation fraction is the boiling point of sevoflurane, which is 58° C. to 59° C. The process of distilling components having lower boiling points before collection of a main distillation fraction corresponds to "collection of a first distillation fraction." As stated above, there is substantially no difference in the boiling point between a compound A and sevoflurane. In fact, the first distillation fraction mainly consists of sevoflurane. It is therefore difficult to set a boundary point between the temperature for collection of a first distillation fraction and the temperature for collection of a main distillation fraction. Accordingly, it is preferable to continuously determine the gas chromatograph composition of each fraction during distillation in an appropriate manner and to continuously collect a "first distillation fraction" while a compound A is detected and then collect a "main distillation fraction" when the compound A is confirmed to be substantially undetectable (less than 1 ppm).

In a preferable embodiment of the present invention, the "first distillation fraction" is used as a starting material (1st organic liquid) in the subsequent step 1a.

[3] Step 1a

Step 1a is a particularly preferable embodiment of step 1 described above. In other words, step 1a is in common with step 1 in terms of "mixing a compound A with HF and water to conduct a reaction". Meanwhile, step 1a is characterized in that a compound A serving as a raw material is provided as a "liquid mixture of sevoflurane and a compound A (1st organic liquid)."

A method for producing a "1st organic liquid" serving as a raw material is not particularly limited; however, it is preferable to use a liquid collected as a "first distillation fraction" during "distillation in step A" described above.

In addition, the "1st organic liquid" is converted to a "2nd organic liquid" in step 1a. As stated above, the "2nd organic liquid" means: (i) an organic liquid containing sevoflurane and a compound A in an amount that is lower than that in the "1st organic liquid;" or (ii) an organic liquid containing sevoflurane and substantially no compound A. A difference between (i) and (ii) is whether conversion of a compound A to a compound X is completed.

The content of a compound A used as a raw material in the "1st organic liquid" in this step is not particularly limited. When the "1st organic liquid" is produced by "step A," the content of a compound A in the "1st organic liquid" depends on the content of a compound A in crude sevoflurane before step A, and it may change depending on conditions for implementation of distillation. The content of a compound A in the "1st organic liquid" is usually 5 ppm to 10000 ppm and typically 10 to 1000 ppm. However, even when the content of a compound A is higher or lower than the above range, it is possible to conduct step 1a. As a result of a decrease in the content of a compound A, advantages of the present invention are achieved to a sufficient extent.

As explained above, a degradation reaction of coexisting sevoflurane is not induced under the conditions of step 1a. In step 1a, sevoflurane, which is the component, remains as is. Meanwhile, a compound A is chemically changed over time so that the compound A is converted to a "compound X" that can be easily separated from sevoflurane. When step 1a is conducted, sevoflurane acts as an internal standard substance. Therefore there is no need to add a standard substance such as DCE. After the start of the reaction, it is possible to understand the status of progress in the reaction by sequentially determining the ratio of gas chromatography areas of sevoflurane and a compound A.

A difference between "step 1" and "step 1a" described above is merely whether or not "sevoflurane that is inert to react" is contained as an essential component. In this regard, the conditions described for "step 1" may be applied again as conditions for "mass ratio of HF and water," "mass ratio of compound A and HF," "reactor material," "method for stirring," "reaction temperature," and the like.

As explained above, as the main component in the "1st organic liquid" serving as a raw material is sevoflurane in the case of step 1a, the absolute amount of a compound A is usually very small. Therefore, in the case of step 1a, the "mass ratio of compound A:HF" tends to be very high, while the compound A is usually diluted with a large amount of sevoflurane. In such case, as explained in the section of step 1 above, it is preferable to set the mass ratio so that the amount of HF is excessively greater than that of the compound A in many cases. Further, the reaction rate in step 1a is also influenced by "mass ratio of HF and water," "method for stirring," and "reaction temperature." Therefore, in order to understand the status of progress in the reaction, it is desirable that the ratio of gas chromatography areas of sevoflurane and a compound A can be sequentially determined, which is preferable upon setting of the primary conditions.

It should be noted that the purpose of "step 1a" according to the present invention is to "reduce" the content of a compound A contained in the "1st organic liquid," which does not necessarily mean that the content needs to be reduced to zero. In other words, in a case in which a certain amount (content) of the compound A can be reduced in the "1st organic liquid" in step 1a, even if distillation is performed in step 2 (described below) at the same number of theoretical stages and the same reflux ratio as in the previous "step A," the amount of a "first distillation fraction" decreases in response to a decrease in the amount of the compound A, thereby making it possible to collect "sevoflurane containing substantially no compound A" as a main distillation fraction. The reaction in step 1a takes very long time to complete the reaction depending on conditions, which might be rather insufficient. Therefore, there is a well-reasonable option to predetermine the time required for step 1a, conduct a reaction at the predetermined mass ratio, stirring method, and reaction temperature and then terminate the reaction step (even if the conversion rate does not reach 100%) within the predetermined time.

For example, step 1a is conducted for preferably 30 minutes to 5 hours and more preferably 30 minutes to 2 hours and then terminated in a preferable embodiment.

In addition, as the reaction in step 1a is a non-uniform liquid-liquid reaction, the presence of a surfactant might promote the reaction. In particular, when hexafluoroisopropyl alcohol (HFIP), which is an amphipathic substance regarded as a surfactant, is allowed to coexist, the rate of reduction in the content of a compound A tends to increase even if the other conditions are the same (see Example 3).

HFIP is a raw material used for sevoflurane synthesis in Patent Literature 1, and therefore, it is often contained in a reaction solution for sevoflurane synthesis. In addition, HFIP itself does not cause degradation of sevoflurane. Therefore, when conducting step 1a, it is particularly preferable to allow HFIP to coexist. When HFIP is used, the amount thereof is preferably 0.001 g to 20 g and more preferably 0.01 g to 10 g per 1 g of sevoflurane in the "1st organic liquid."

In one particularly preferable embodiment, HFIP is allowed to coexist and a reaction (the contact described above) is conducted at 0° C. to 60° C. in step 1a of the present invention. When the reaction is conducted under such conditions, it tends to result in acceleration of degradation of, in particular, a compound A into a compound X. Step 1a conducted under such conditions is sometimes herein referred to as "step 1b" as explained above.

Step 1a may be conducted under the presence of sulfuric acid. As sulfuric acid is also a raw material used for synthesis of sevoflurane by the method disclosed in Patent Literature 1, it is often contained in a reaction solution after termination of the reaction. The present inventors have found that when step 1a of the present invention is conducted, the coexistence of sulfuric acid does not particularly inhibit the reaction, and there is no fact that a by-product that is difficult to separate from sevoflurane is generated. However, if the amount of sulfuric acid ($H_2SO_4$) is extremely large, it might cause inactivation of "water" necessary for step 1a. Therefore, it is not preferable that the mass of sulfuric acid is remarkably greater than the mass of water, for example. Usually, sulfuric acid in such an extremely large amount is not introduced into a reaction system. However, in a case in which the amount of sulfuric acid is large due to some reasons, it is preferable to allow water to be present at a mass that is at least equal to and preferably 2-fold or more that of sulfuric acid.

After the termination of step 1a, two-layer separation may be conducted according to an ordinary method so that an organic layer can be collected. The thus collected organic layer is a "2nd organic liquid." The "2nd organic liquid contains sevoflurane as a main component as in the case of the "1st organic liquid" serving as a raw material; however, the content of the compound A in the 2nd organic liquid is significantly lower than that in the "1st organic liquid." Note that as the organic layer usually includes HF used in step 1a, it is preferable to conduct a purification operation such as washing with an alkaline aqueous solution or water washing for the collected organic layer in order to reduce a load to a system used in the subsequent step 2 (distillation). Specifically, it is desirable to conduct either washing with an alkaline aqueous solution or water washing at least once.

[4] Step 2 (Distillation in Step 2)

Step 2 is a step of distilling the "2nd organic liquid" obtained in step 1a (or "step 1b" that is a particularly preferable embodiment of step 1) under the presence of a degradation inhibitor so as to obtain, as a main distillation fraction, sevoflurane containing substantially no compound A. In order to distinguish distillation in this step from "distillation in step A" described above, distillation in this step is sometimes herein referred to as "distillation in step 2." Note that subject matter obtained through "distillation in step A" is a "first distillation fraction" while subject matter obtained through "distillation in step 2" is a "main distillation fraction."

As described in detail above, as a result of the reaction of step 1a, the content of the compound A in the "2nd organic liquid" is significantly lower than that in the "1st organic liquid." Therefore, it is possible to additionally collect, as a main distillation fraction, "sevoflurane containing substantially no compound A" by distilling the "2nd organic liquid" in step 2 under, for example, the same conditions of "distillation in step A" (in terms of the number of theoretical stages, reflux ratio, or the like).

Since "distillation in step 2" is in common with "distillation in step A" in terms of "distillation of sevoflurane," the conditions described in detail in the section of "distillation in step A" may be applied again as the conditions of distillation in step 2 (type or amount of a degradation inhibitor, a distiller, the number of theoretical stages, the reflux ratio, distillation pressure, and temperature). Note that distillation in step 2 is different from "distillation in step A" in that subject matter of step 2 is not a first distillation fraction but a main distillation fraction. In other words, a "first distillation fraction" may be collected while the component A is detected as a fraction during distillation, and when the compound A becomes uncollectable, a "main distillation fraction" may be collected.

When conducting "distillation in step A" prior to distillation in step 2, it is typical to conduct "distillation in step 2" under the same conditions of "distillation in step A", which is particularly rational. This is because both steps have in common that sevoflurane is distilled so that sevoflurane is obtained as a main distillation fraction. In other words, the point of distillation in step 2 is to recover sevoflurane to a possible extent as a "main distillation fraction" from the first distillation fraction under conditions that have already been optimized in step A. Therefore, it is not necessary to significantly increase the number of theoretical stages or the like instead of optimizing conditions of "distillation in step A" so as to conduct distillation in a more strict manner for a longer period of time. Note that, if desired, "distillation in step 2" may be conducted under more strict conditions.

On the other hand, in a case in which distillation is conducted under distillation conditions which are less strict than those of "distillation in step A" (meaning that the number of theoretical stages or the reflux ratio is reduced), it might be impossible to collect a "main distillation fraction" (sevoflurane containing substantially no compound A) even by conducting "distillation in step 2," although it depends on the degree of reduction of the compound A in step 1a. In a case in which the main distillation fraction cannot be collected by conducting distillation in step 2 under such less strict conditions, reduction of the compound A via the reaction in step 1a becomes meaningless, which is not preferable. Meanwhile, in a case in which there is a remarkable decrease in the compound A as a result of step 1a, distillation would be possible even by making distillation conditions of "distillation in step 2" less strict than those of "distillation in step A." In such case, it is advantageous in that distillation in step 2 can be more easily conducted. In other words, optimal conditions of "distillation in step 2" are determined also depending on the conditions of the previous step 1a. It is therefore preferable to adjust conditions based on the knowledge of those skilled in the art by checking the degree of collection of sevoflurane as a main distillation fraction.

As stated above, although there is no particular limitation in conditions of "distillation in step 2," it is possible to save labor in the distillation step and effectively use a distillation system by conducting "distillation in step 2" under the same conditions (for example, using the same distillation column) of the previously conducted "distillation in step A," which can be a preferable embodiment.

Sevoflurane recovered as a "main distillation fraction" in "distillation in step 2" can be added to a sevoflurane product. Specifically, the thus recovered "main distillation fraction" is sevoflurane that could not be collected in step A, meaning that sevoflurane can be recovered by step 2 as a result of the previous step 1a.

A "first distillation fraction" is also collected during "distillation in step 2." The "first distillation fraction" is a "sevoflurane containing a compound A at a significant level"

as in the case of the first distillation fraction in step A (even if the "2nd organic liquid" serving as a raw material for distillation in step 2 contains no compound A, a minute amount of a compound A can be generated through distillation). This "first distillation fraction" may be discarded because its amount is relatively small. Alternatively, it may be collected so as to be reused as a raw material in "step 1a" (1st organic liquid).

Meanwhile, residues (tank bottom) remaining after collection of a main distillation fraction during distillation in "step 2" is herein referred to as a "3rd organic liquid." This "3rd organic liquid" may be discarded. The present inventors, however, found that the "3rd organic liquid" contains "polyether" that can be a raw material of sevoflurane. Therefore, if desired, "step 3" described below can be conducted using the "3rd organic liquid" as a raw material.

As stated above, typical examples of "polyether" used herein are "polyether 1" and "polyether 2." Usually, these polyethers are generated in large amounts. When the time or temperature for distillation in step 2 is prolonged or increased, "polyether 3" and "polyether 4" tend to be generated, in addition to or instead of these polyethers.

[5] Step 3

Step 3 is a step of bringing the "3rd organic liquid" obtained as tank bottom after step 2 into contact with anhydrous HF and a reaction accelerator (particularly preferably sulfuric anhydride), thereby obtaining a "4th organic liquid" in which at least a part of "polyether" in the "3rd organic liquid" is converted to sevoflurane.

As stated above, there are various types of "polyether" in the 3rd organic liquid after the termination of distillation in step 2. Usually, the 3rd organic liquid is in the form of a mixed composition of different types of polyethers. However, regardless of abundance of specific chemical species of polyether, polyethers can be converted to sevoflurane by bringing the "3rd organic liquid" into contact with anhydrous HF and a reaction accelerator in accordance with the disclosure of JP Patent No. 3441735. In most cases, the amount of the 3rd organic liquid collected is smaller than that of the "1st organic liquid" serving as a raw material in step 1a. Therefore, it is also possible to conduct step 3 after conducting steps 1 and 2 for a plurality of batches so as to achieve a certain recovery amount of the 3rd organic liquid.

Examples of the reaction accelerator include: Brønsted acids such as fuming sulfuric acid, concentrated sulfuric acid, sulfuric acid, fluorosulfuric acid, anhydrous phosphoric acid, phosphoric acid, and trifluoromethanesulfonic acid; and Lewis acids such as titanium tetrachloride, aluminium chloride, antimony pentachloride, aluminium trifluoride, sulfuric anhydride, and antimony pentafluoride. Of these, fuming sulfuric acid, concentrated sulfuric acid, sulfuric acid (80% by weight or more), fluorosulfuric acid, phosphoric acid, or a mixture thereof is preferable. Concentrated sulfuric acid is particularly preferable.

The reaction temperature is not particularly limited; however, it is 10° C. to 100° C. and preferably 35° C. to 80° C. Generated sevoflurane can be distilled with an unreacted raw material outside of a reaction system within the above temperature range, which is preferable. When the reaction temperature is below 10° C., the reaction is decelerated, which is not practical, and when it is above 100° C., the reaction is excessively accelerated, making it difficult to control the reaction, which is not preferable.

As the reaction pressure does not substantially influence the reaction, it is not particularly limited. Usually, the reaction may be conducted at 0.1 to 1 MPa.

The reaction of step 3 may also be conducted under the presence of formaldehyde or paraformaldehyde.

The mixing ratio of reaction reagents used in the method of the present invention is specified as follows: a: when formaldehyde is used, the molar number of formaldehyde is added to the total molar number of an oxymethylene group of "polyether" in the "3rd organic liquid;" b: when HFIP is used in combination, the molar number of HFIP is added to the molar number of a hexafluoroisopropenyl group of "polyether" in the "3rd organic liquid;" c: the molar number of HF; d: the molar number of a reaction accelerator.

The value of b/a is usually 0.5 to 5 and preferably 0.7 to 3.

The value of c/a is usually 1 to 50 and preferably 3 to 30 (it is preferable for HF to exist at at least an equimolar level with respect to an oxymethylene group in order to improve reaction yield).

Here, d represents the molar number of an arbitrary component. When an arbitrary component is used, the value of d/a is usually 0.5 to 20 mol times and preferably 0.7 to 5.0 mol times.

Preferably, no water exists in step 3. It is not required to strictly control the moisture concentration using a Karl Fischer moisture titrator; however, it is not preferable to actively add water to the reaction system as in the case of step 1 or step 1a. The amount of water is desirably 0.01 mol or less when the "a" above is 1 mol. In addition, when fuming sulfuric acid, sulfuric anhydride, or the like is used as a reaction accelerator, even if a minute amount of water exists in the reaction system, such reaction accelerator captures (inactivates) water, resulting in substantially anhydrous conditions, which is preferable.

In addition, as in the case of step 1 or step 1a, the reaction in step 3 efficiently proceeds during stirring, which is preferable.

An embodiment of the reaction in step 3 is not particularly limited. The reaction proceeds under either tight sealing conditions or open conditions so that a "4th organic liquid" in which at least a part of "polyether" in the 3rd organic liquid is converted to sevoflurane can be obtained over time.

When the reaction is conducted under open conditions, a sevoflurane product has a boiling point of 58° C. to 59° C., at which the reaction in step 3 can proceed to a sufficient extent. Therefore, a technique of mixing the 3rd organic liquid, hydrogen fluoride, the reaction accelerator as mentioned above (particularly preferably concentrated sulfuric acid), and if necessary, paraformaldehyde at certain amounts and gradually increasing the temperature to cause a reaction around 60° C. is preferable. Once sevoflurane is generated, sevoflurane quickly becomes vapor at such temperature. By capturing such vapor using a water cooling trap or the like, it is possible to collect generated sevoflurane. Sevoflurane collected by such method is crude sevoflurane, and therefore, it may contain HF or polyether as a reaction material; however, high-boiling point components can be removed. Therefore, it is preferable to collect crude sevoflurane by such technique (crude sevoflurane obtained by collecting vapor in the above manner falls within the scope of the "4th organic liquid").

As the "4th organic liquid" obtained above usually includes HF used as a raw material, it is preferable to conduct a purification operation such as washing with an alkaline aqueous solution or water washing for the collected organic layer in order to reduce a load to a system used in the subsequent step 4 (distillation). Specifically, it is desirable to conduct washing with an alkaline aqueous solution or water washing at least once.

[6] Step 4 (Distillation in Step 4)

Step 4 (distillation in step 4) is a step of obtaining sevoflurane containing substantially no compound A as a main distillation fraction by distilling the "4th organic liquid" obtained in step 3 under the presence of a degradation inhibitor.

This step may be conducted in the manner of step 2 except that the amount of a subject to be distilled is smaller than that in step 2 (distillation in step 2). The type or amount of a degradation inhibitor, the number of theoretical stages of distillation, a method for switching collection of a first distillation fraction to collection of a main distillation fraction, and other conditions described in step 2 can be applied again to this step.

The amount of the "4th organic liquid" collected is smaller than that of the "2nd organic liquid" serving as a raw material in step 2. Therefore, it is also possible to conduct step 4 after conducting steps 1 and 2 for a plurality of batches to achieve a certain recovery amount of the 4th organic liquid. However, in this step, as long as it is possible to distill the 4th organic liquid to collect high-purity sevoflurane (sevoflurane containing substantially no compound A), a specific method of the operation is not limited.

EXAMPLES

The present invention will be described more in detail below with reference to the following Examples. However, the present invention is not limited thereto.

Example 1

(Step 1)

A compound A (purity: 99% or more) (5 g), HF (20 g), water (100 g), and 1,2-dichloroethane (DCE) serving as an internal standard substance (15 g) were mixed, followed by stirring in an air-tight polytetrafluoroethylene resin container for 5 hours at 20° C. to 25° C., thereby conducting a reaction. During the reaction, the peak area ratio of [compound A]/[DCE] was determined by FID gas chromatograph analysis at 1-hour intervals. Note that a sample liquid was brought into contact with NaF for dehydrofluorination and then analyzed by gas chromatography (the retention time for the compound A was around 5.2 minutes and the retention time for DCE was around 16.5 minutes under the gas chromatography conditions).

As a result, although the peak area ratio of [compound A]/[DCE] was 0.57 immediately before the start of the reaction, it became 0.48, 0.38, 0.31, 0.25, and 0.19 in 1, 2, 3, 4, and 5 hours, respectively, after the start of the reaction. In other words, after the elapse of 5 hours, the peak area ratio decreased to one-third of the original level. No specific main peak was detected as a product peak; however, it was confirmed that the compound A was chemically changed in step 1.

In addition, sevoflurane was not significantly detected in the reaction mixture. It was found that the above operation does not substantially convert the compound A to sevoflurane.

Example 2

(Step A)

The standard substance of the compound A (used in Example 1) was used so that "sevoflurane containing compound A at 100 ppm" was prepared. The obtained sevoflurane (1000 g) was introduced into a glass distillation tank. In addition, a 1% sodium hydrogen phosphate aqueous solution (70 g) was added thereto, followed by ordinary pressure distillation using a distillation column with 10 theoretical stages at a reflux ratio of 5 to 20.

The distillate was analyzed by FID gas chromatography and collected as a "first distillation fraction" while the compound A was detectable at 1 ppm or more. Then, when the compound A was detected at a level of less than 1 ppm, the distillate was collected as a "main distillation fraction."

As a result, the recovered amount of the "first distillation fraction" was 267 g, in which the content of compound A was 341 ppm. Meanwhile, the recovered amount of the "main distillation fraction" was 720 g, in which no compound A was detected (less than 1 ppm) (collection yield of the main distillation fraction=72%).

(Step 1a)

The "first distillation fraction (content of compound A: 341 ppm)" obtained above (step A) (240 g) was introduced into a stainless-steel autoclave, and an "HF aqueous solution (prepared by dissolving 10 g of anhydrous HF in 50 g of water)" was added. The autoclave was closed, followed by stirring using a stirrer (reaction temperature=20° C. to 25° C.).

The reaction was terminated 5 hours after the start of the reaction. The organic layer inside the autoclave was recovered and washed with water. Then, the organic layer was analyzed by gas chromatography. As a result, the content of compound A was 123 ppm. In other words, the content of compound A significantly decreased after the elapse of 5 hours (conversion rate: 63%). The total amount of the remaining organic layer was washed with a "sodium hydroxide aqueous solution" so that acids were removed.

(Step 2)

The total amount of the organic layer (after washing) obtained above (step 1a) was introduced into a stainless-steel distiller, 17 g of a 1% sodium hydrogen phosphate aqueous solution was added thereto, followed by ordinary pressure distillation using a distillation column with 10 theoretical stages at a reflux ratio of 5 to 20.

The distillate was analyzed by FID gas chromatography and collected as a "first distillation fraction" while the compound A was detectable at 1 ppm or more. Then, after the compound A was confirmed to be at less than 1 ppm, the distillate was collected as a "main distillation fraction."

As a result, 76 g of the "first distillation fraction" was recovered, in which the content of compound A was 330 ppm. Meanwhile, 128 g of the "main distillation fraction" was recovered, in which no compound A was detected (less than 1 ppm). As described in "Comparative Example 1" below, it was found that it is impossible to obtain the main distillation fraction by simply distilling the first distillation fraction obtained above (step A). Meanwhile, in this step (step 2), the main distillation fraction (in an amount that was not large but at a significant level) was successfully recovered. This is probably because that the content of compound A could be reduced in the above step (step 1a).

In addition, 31 g of "tank bottom" (note that all of the components having boiling points higher than the boiling point of the main distillation fraction were considered to be "tank bottom") was obtained. The "tank bottom" was analyzed by FID gas chromatography. As a result, "polyether 1," "polyether 2," "polyether 3," and sevoflurane were detected at 42%, 6%, 1%, and 20%, respectively (while no compound A was detect). In addition, detected sevoflurane was considered to be sevoflurane which had not been distilled but had remained in the tank during distillation other than sevoflurane which had been generated via the reaction during distillation.

(Steps 3 and 4)

The "tank bottom" (31 g) obtained in step 2 was introduced into a stainless-steel autoclave, and 98% sulfuric acid (100 g) and hydrogen fluoride (200 g) were added thereto. The mixture was gradually heated for 4 hours to 65° C.

Vapor generated during the reaction was captured using a water trap, and the obtained organic layer was washed with water. The organic matter (26 g) was recovered.

The obtained organic matter was analyzed by FID gas chromatography. This organic matter was found to contain sevoflurane at 96.3%.

The organic matter was washed with aqueous sodium hydroxide, followed by distillation under the conditions described in step 2. Accordingly, 14 g of sevoflurane (purity: 99.9% or more) was obtained.

As described above, by conducting steps 3 and 4 in combination, it was possible to further recover high-purity sevoflurane, which had been impossible to collect by conventional techniques.

Example 3

(Step 1b)

In Example 3 and the subsequent examples, a reaction corresponding to step 1b was conducted at a small scale (one-tenth scale of Example 2) as a model experiment similar to step 1a of Example 2 (using a small sealable stainless-steel reactor).

At first, the standard substance of compound A and sevoflurane were mixed so that "sevoflurane containing compound A at 340 ppm" was prepared. The sevoflurane was designated as a reaction material in Example 3 and the subsequent examples.

An "HF aqueous solution (prepared by dissolving 1.0 g of anhydrous HF in 5.0 g of water)" was added to 24 g of the "sevoflurane containing compound A at 340 ppm." Further, 1.0 g of HFIP was added and an autoclave was closed. Stirring was initiated using a magnetic stirrer and the interior temperature was maintained at 20° C. to 25° C.

After the elapse of 5 hours, FID gas chromatography was conducted for determination. The conversion rate of compound A was estimated as 73%. As HFIP was added, the conversion rate was slightly improved from 63% to 73%, compared to Example 2.

Example 4

A reaction corresponding to step 1b was conducted by further adding 1.0 g of concentrated sulfuric acid under the conditions described in step 1b of Example 3.

After the elapse of 5 hours, FID gas chromatography was conducted for determination. The conversion rate of compound A was estimated as 71%. In other words, the results of Example 4 were not largely different from those of Example 3. It was found that the reaction would not be inhibited even under the presence of sulfuric acid.

Example 5

A reaction corresponding to step 1b was conducted under the conditions described in step 1b of Example 4 at a reaction temperature of 45° C.

After the elapse of 5 hours, FID gas chromatography was conducted for determination. The conversion rate of compound A was 81%. It was found that an increase in the temperature would cause a certain increase in the reaction rate.

Comparative Example 1

"Step A" of Example 2 was repeated at the same scale under the same conditions. As a result, 260 g of the "first distillation fraction" (content of compound A=350 ppm) was recovered. The total amount of this first distillation fraction was directly subjected again to ordinary pressure distillation (the number of theoretical stages was set to 10 and the reflux ratio was set to 5 to 20 as in "step A" of Example 2) without step 1a with the addition of 18 g of a 1% sodium hydrogen phosphate aqueous solution.

However, the detection level of the compound A did not decrease to a level "below the detection limit (1 ppm)" under the above conditions. As a result, the "main distillation fraction" was not recovered. In other words, it was found that it is impossible to recover high-purity sevoflurane by simply repeating distillation of the "first distillation fraction" without step 1a.

Comparative Example 2

Attempts were made to conduct a reaction as described above using the same reaction materials and the same reaction container by bringing "the compound A (5 g) and anhydrous HF (20 g)" into contact with each other without the addition of "water (100 g)" used as a reaction material in "Example 1 (step 1)" above (with the use of 1,2-dichloroethane (DCE) (15 g) as an internal standard substance).

The peak area ratio of [compound A]/[DCE] was 0.57 immediately before the start of the reaction. However, as a result of determination of the peak area ratio of [compound A]/[DCE] by FID gas chromatography analysis 5 hours later, the peak area ratio of [compound A]/[DCE] remained almost unchanged (0.56). Thus, it was considered that the compound A practically does not react under anhydrous conditions.

INDUSTRIAL APPLICABILITY

The present invention is advantageous in that a compound A can be converted to a compound X, which can be easily separated from sevoflurane (step 1).

In addition, in another embodiment, the present invention is advantageous in that it is possible to selectively allow the compound A in a "1st organic liquid" to react, thereby producing a "2nd organic liquid" containing a reduced content of the compound A or containing substantially no compound A (step 1a).

Further, in still another embodiment, the present invention is advantageous in that it is possible to produce sevoflurane containing substantially no compound A at a significantly large amount compared with the case of not conducting step 1a using, as a raw material, the "1st organic liquid" which has been conventionally difficult to effectively use (step 1a and step 2).

Furthermore, in still another embodiment, the present invention is further advantageous in that it is surprisingly possible to produce sevoflurane using, as a raw material, residues (tank bottom) remaining after distillation in step 2 (step 1a and steps 2 to 4).

According to the present invention, it becomes possible to produce sevoflurane using, as a starting material, "sevoflurane containing a compound A (1st organic liquid)" which has been difficult to effectively utilize, thereby providing an improved method for producing sevoflurane.

The invention claimed is:

1. A method for reducing the amount of a compound A, wherein the compound A is fluoromethyl-1,1,3,3,3-pentafluoroisopropenyl ether, in a solution, comprising bringing compound A into contact with a composition containing hydrogen fluoride and water at a mass ratio of 1:1 to 1:30.

2. A method for reducing the amount of a compound A, wherein the compound A is fluoromethyl-1,1,3,3,3-pentafluoroisopropenyl ether, in a solution containing sevoflurane and the compound A, comprising bringing a liquid containing sevoflurane and compound A into contact with a composition containing hydrogen fluoride and water at a mass ratio of 1:1 to 1:30, thereby, obtaining (i) an organic liquid containing sevoflurane and the compound A in an amount that is lower than that in the 1st organic liquid; or (ii) an organic liquid containing sevoflurane and less than 1 ppm of compound A.

3. The method according to claim 2, wherein a temperature during the contact is 0° C. to 60° C.

4. The method according to claim 2, wherein the contact is made under the coexistence of hexafluoroisopropyl alcohol.

5. A method for producing sevoflurane containing less than 1 ppm of compound A, comprising the following step:
    step 2 of distilling the organic liquid obtained by the method according to claim 2 under the presence of a degradation inhibitor, thereby obtaining the sevoflurane containing less than 1 ppm of compound A as a main distillation fraction.

6. The method according to claim 5, wherein the degradation inhibitor used in step 2 is at least one member selected from the group consisting of $NaHCO_3$, $Na_2B_4O_7$, $H_3BO_4$, $C_6H_4(COOK)(COOH)$, $Na_2SO_3$, $Na_2HPO_4$, $CH_3COONa$, and $Na_3PO_4$.

7. The method according to claim 5, further comprising the following step:
    step 3 of bringing anhydrous hydrogen fluoride and a reaction accelerator into contact with a 3rd organic liquid as residues remaining after distillation in the step 2, thereby obtaining a 4th organic liquid in which at least a part of a component in the 3rd organic liquid is converted to sevoflurane.

8. The method according to claim 7, further comprising the following step:
    step 4 of distilling the 4th organic liquid so as to obtain sevoflurane containing less than 1 ppm of compound A as a main distillation fraction.

9. The method according to claim 2, wherein the "liquid" is obtained as a first distillation fraction in the following step:
    step A of distilling sevoflurane under the presence of a degradation inhibitor so as to collect the first distillation fraction.

10. The method according to claim 9, wherein the degradation inhibitor used in step A is at least one member selected from the group consisting of $NaHCO_3$, $Na_2B_4O_7$, $H_3BO_4$, $C_6H_4(COOK)(COOH)$, $Na_2SO_3$, $Na_2HPO_4$, $CH_3COONa$, and $Na_3PO_4$.

11. A method for producing sevoflurane containing less than 1 ppm of compound A, wherein the compound A is fluoromethyl-1,1,3,3,3-pentafluoroisopropenyl ether, comprising the following steps:
    step 1b of bringing a liquid (1st organic liquid containing sevoflurane and compound A into contact with a composition containing hydrogen fluoride and water at a mass ratio of 1:1 to 1:30 under the presence of hexafluoroisopropyl alcohol at 0° C. to 60° C., thereby obtaining the following 2nd organic liquid (i) or (ii): (i) an organic liquid containing sevoflurane and the compound A in an amount that is lower than that in the 1st organic liquid; or (ii) an organic liquid containing sevoflurane and less than 1 ppm of compound A; and
    step 2 of distilling the 2nd organic liquid under the presence of a degradation inhibitor, thereby obtaining the sevoflurane containing less than 1 ppm of compound A as a main distillation fraction.

12. The method according to claim 11, further comprising the following steps:
    step 3 of bringing a 3rd organic liquid as residues remaining after distillation in step 2 into contact with anhydrous hydrogen fluoride and a reaction accelerator, thereby obtaining a 4th organic liquid in which at least a part of the 3rd organic liquid is converted to sevoflurane; and
    step 4 of distilling the 4th organic liquid under the presence of a degradation inhibitor, thereby obtaining sevoflurane containing less than 1 ppm of compound A as a main distillation fraction.

13. The method according to claim 12, wherein the 1st organic liquid is a first distillation fraction obtained by
    distilling sevoflurane under the presence of a degradation inhibitor, thereby collecting a first distillation fraction.

* * * * *